United States Patent [19]

Ams et al.

[11] Patent Number: 5,091,779
[45] Date of Patent: Feb. 25, 1992

[54] AUTOMATIC LIGHT ADJUSTMENT MEANS FOR AN ENDOSCOPE

[75] Inventors: Felix Ams, Kämpfelbach; Roland Schäfer, Bretten-Dürrenbüchig, both of Fed. Rep. of Germany

[73] Assignee: Richard Wolf GmbH, Knittlingen, Fed. Rep. of Germany

[21] Appl. No.: 551,702

[22] Filed: Jul. 11, 1990

[30] Foreign Application Priority Data

Aug. 25, 1989 [DE] Fed. Rep. of Germany ....... 3928052

[51] Int. Cl.⁵ .............................................. A61B 1/04
[52] U.S. Cl. .................................. 358/98; 358/168; 128/6
[58] Field of Search ............. 358/98, 168; 128/4, 128/6

[56] References Cited

U.S. PATENT DOCUMENTS

| | | | |
|---|---|---|---|
| 3,257,506 | 5/1966 | Siepmann | 178/6.8 |
| 4,423,436 | 12/1983 | Kimura | 358/98 |
| 4,628,362 | 12/1986 | Waehnee | 358/169 |
| 4,688,087 | 8/1987 | Ams et al. | 358/100 |
| 4,834,071 | 5/1989 | Hosoi et al. | 358/98 |
| 4,963,960 | 10/1990 | Takami | 358/98 |
| 4,967,269 | 10/1990 | Sasagawa et al. | 358/169 |

FOREIGN PATENT DOCUMENTS

3743090 7/1988 Fed. Rep. of Germany.
3818125 12/1988 Fed. Rep. of Germany.

*Primary Examiner*—James J. Groody
*Assistant Examiner*—Kim Yen Vu
*Attorney, Agent, or Firm*—Panitch Schwarze Jacobs & Nadel

[57] ABSTRACT

Apparatus for adjusting the quantity of light emitted by a light source for illuminating an object under examination by means of an endoscope fitted with a video camera, comprises a signal processing circuit including a window generating device and a window superimposition device for visually displaying and optically defining a window and which generates a measuring window in the video picture displayed by a monitor connected to the video camera and superimposes the measuring window on the video picture in the form of a frame. A video signal for adjusting the quantity of light emitted by the light source is integrated only within the measuring window.

3 Claims, 1 Drawing Sheet

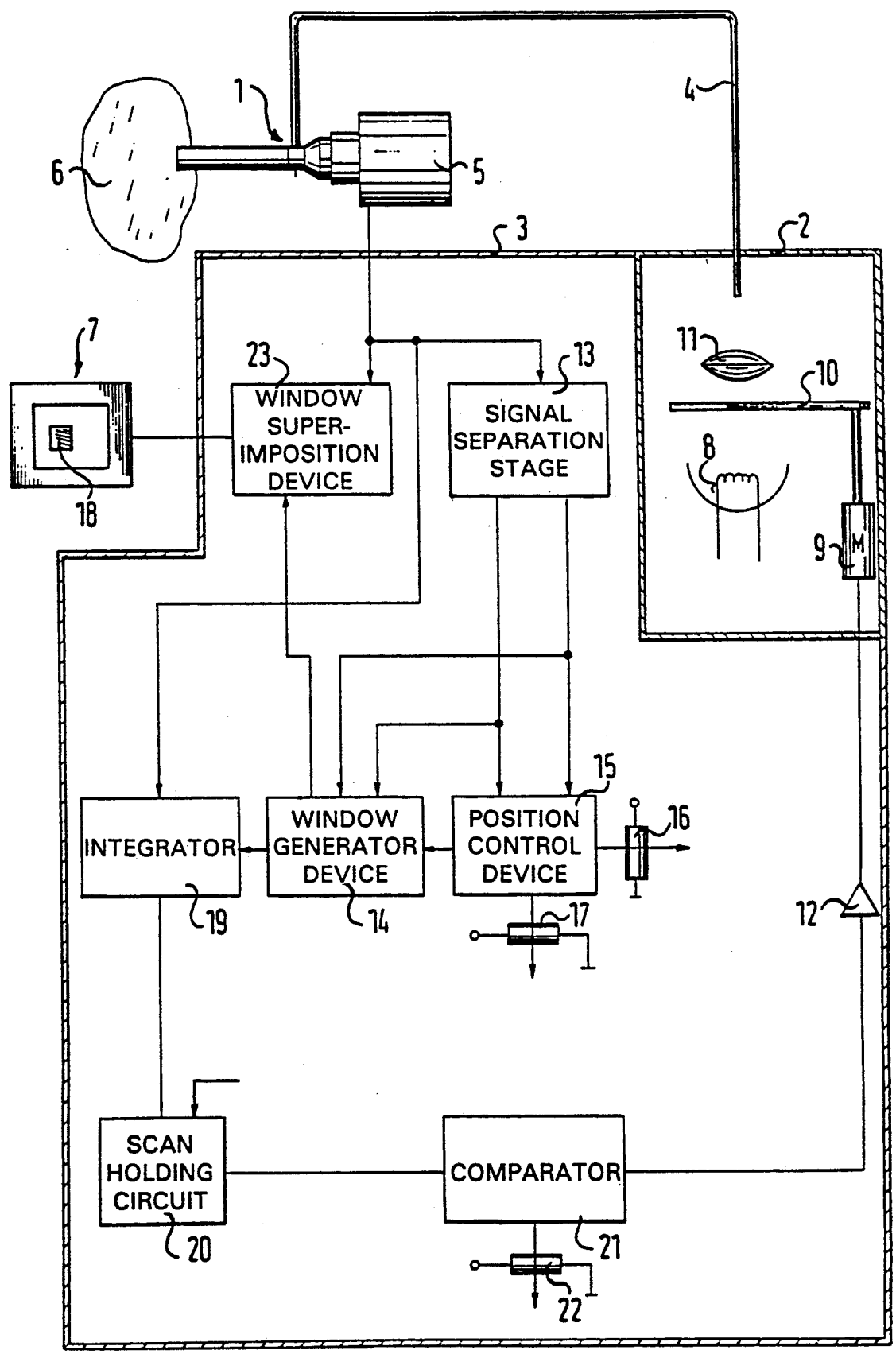

AUTOMATIC LIGHT ADJUSTMENT MEANS FOR AN ENDOSCOPE

FIELD OF THE INVENTION

The invention relates to apparatus for the automatic adjustment of a source of light for illuminating an object under examination by means of an endoscope, comprising a light guide for transmitting the light to bring it to bear on said object; an image guide connected to a video camera; and a system for processing the signals produced by the video camera.

BACKGROUND OF THE INVENTION

Endoscopes are commonly used for examining relatively inaccessible objects, for example in body cavities. For evaluating and documenting an object being examined, an externally connected camera may be provided for depicting a part of the body which is under examination. The camera may be a photographic camera, or if a light converter element, for example a CCD, is provided, for converting optical signals into electrical video signals, a video recorder may be used. In order to produce recordings enabling exact diagnosis, optimum illumination of the object examined must be provided for. If a constant quantity of light is supplied by the light source to the object examined, some regions under examination which are highly reflective may be overexposed and others which are less reflective may be underexposed. The light source should, therefore, be automatically adjustable to ensure the optimum quantity of light at variable ranges.

A control circuit for adjusting the intensity of a light source is described, for example, in DE-B 35 09 825, wherein a light projector of adjustable luminous intensity, enables the intensity of the illumination of an object examined to be set according to the distance of the object from the distal end of an endoscope, and limited to a maximum value. This is accomplished by comparing required and actual values of a video signal, taking the maximum permissible amplitude of the video signal as the required value. Such peak value control ensures that the brightest parts of the video picture do not overexpose. The background of the picture is usually too dark, however.

According to DE-B 31 18 341 the pictures are taken by means of a television camera. The quantity of light applied to the light guide is controlled so that the voltage of the video signal is held to an essentially constant level irrespective of changes in the distance between the object under examination and the distal end of the endoscope. Since the mean value of the video signal is used for controlling the brightness of the picture, the object under examination is not always correctly lit.

As described in DE-A 37 43 090, the illuminating light and the brightness of the object depicted are automatically adjusted independently of the size of the picture that can be transmitted by way of the image guide. Alterations in the level of the video signal, resulting from the use of endoscopes having image circles of different diameters and thus different picture ranges, is taken account of by scanning the picture width of the endoscopic image line by line and storing the greatest width of the image as a voltage level by means of a peak value holding circuit and adding it to the actual value of the video signal.

According to DE-A 38 18 125, account is taken of the change in the diameter of the image circle resulting from the use of endoscopes having different diameters and the quantity of light applied to the object examined is adjusted accordingly. This is done by checking the signal levels of pixels of a solid-state video pickup device to determine whether they exceed a specified darkness value, thereby to establish the scanning area corresponding to the area of the cross-section of the image guide. By selection of a correction signal, a light-adjusting signal is generated which adjusts the quantity of light that is fed to the light guide. A square area shown as hatched in the drawing of the reference under discussion, and not the actual image circle area of the endoscope, is used for adjusting the video signal.

US-A-4,628,362, describes a "follow-up control" of an analogue-digital converter for optimum use of the input voltage range of the video signal. An active window is defined in the video picture area. A signal is derived from said active window whereby the full dynamic range of the analogue-digital converter is utilized. The reference under discussion does concern light quantity control and window area detection.

SUMMARY OF THE INVENTION

The present invention is intended to provide for the automatic adjustment of the illuminating light source of an endoscope, so as to assure optimum lighting of the object examined, for video pickup, both where the distance of the object from the distal end of the endoscope varies and independently of the diameter of the image circle of the endoscope which is being used.

According to the present invention the signal processing system is provided with a switchable window generating circuit, which inscribes a measuring window within the video picture picked up by the video camera and controls an integrator so that the video signal used for adjusting the quantity of light applied to the object being examined is only integrated within the measuring window. A manually operable position control may also be provided, for positioning the measuring window within the video picture and also for altering the size of window.

In order to indicate to the user which part of the picture has been selected for brightness control, a window superimposition device may be provided, allowing the measuring window to be superimposed on the video picture in the form of a frame.

BRIEF DESCRIPTION OF THE DRAWINGS

The single Figure is a block schematic diagram of apparatus for automatically adjusting a source of light for illuminating a part of the body under examination by means of an endoscope.

DETAILED DESCRIPTION OF THE INVENTION

The apparatus comprises an endoscope 1, a light source device 2 for supplying the endoscope with light for illuminating a part of the body under examination, and an electronic signal processing system 3. A light guide cable 4 is provided for conducting light from the light source device 2 to the distal end of the endoscope 1. The endoscope 1 is equipped with a video camera 5 which receives, by way of the endoscope 1, an image of the part of a body cavity 6, which is under examination, and converts said image into a video signal which is fed to the signal processing system 3 and to a monitor 7.

The monitor 7 displays the video signal as a picture of the part under examination.

The light source device 2 comprises a light source in the form of an electric lamp 8, an electric motor 9, an apertured plate 10 and a lens device 11 for focusing and filtering the light emitted by the lamp 8 for its transmission by the light guide 4 to the endoscope 1. The motor 9 is connected to the plate 10 for opening and closing its aperture according to the quantity of light that is needed to illuminate the cavity 6. The motor 8 is controlled by control signals generated in the processing system 3, which are applied to a motor drive 12 for controlling the speed and direction of rotation of the motor 9 and thus the speed with which, and the extent to which, the aperture in the plate 10 is opened or closed.

In the processing system 3, the horizontal and vertical synchronization signals are filtered out of the video signal emitted by the camera 5 by means of a synchronization signal separation stage 13 and are fed to a window generator device 14 and a position control device 15. These synchronization signals drive a first line counter for counting the picture lines in the device 15. The count of a first comparative counter clocked by an oscillator can be raised or lowered by means of a first controller 16, thus enabling the vertical position of the measuring window 18 to be established. When the counts of the first line counter and the first comparative counter are equal, a first adjustable timing element is triggered by a first comparator in the window generator device 14. The setting of the first timing element corresponds to the height of the measuring window 18.

The horizontal synchronization signal drives a picture element counter clocked by a picture element oscillator. A second comparative counter clocked by the picture element oscillator can be used for raising or lowering the count by means of a controller 17 to establish the horizontal position of the measuring window 18. When the counts of the picture element counter and the second comparative counter are equal, a second adjustable timing element is triggered by a second comparator in the window generator device 14. The setting of the second timing element corresponds to the width of the measuring window 18.

The outputs of the first and second timing elements are linked in the window generator device 14 by a first AND gate and are fed to an integrator 19, the integration time, and time constant, of which is controllable, where said outputs are linked by a second AND gate to a measuring window selector circuit. When the aperture in the plate 10, and thus the quantity of light, is to be adjusted and the window is to be measured, the integrator 19 integrates the video signal only within the area of the measuring window 18.

At the end of one field, the final integration value is stored in a scan holding circuit 20 and is supplied as an actual value to a required value/actual value comparator 21 and the integrator 19 is then cancelled. The result of the comparison between said actual value and a required value which is preselected by the user by means of a controller 22, is fed to the motor drive 12 which controls the motor 19 and thus the extent of the aperture in the plate 10. The signal outputs of said first and second timing elements of the window generator device 14 are applied to a window superimposition device 23 which superimposes a frame on the video picture corresponding to the window 18, which indicates to the user which part of the picture has been selected for brightness control.

By virtue of the apparatus described above selection can be made between mean value control over the whole of the area of the picture or over a variable window area. The brightness control with measurement of the window does not begin until the area of the window 18 has been selected. Continual fluctuations in brightness as the window area changes are thereby avoided.

Means are provided for manually adjusting the aperture in the plate 10 and thus the quantity of light emitted by the light source device 2, in case the automatic brightness adjustment means should fail. Means are further provided for switching over to manual operation should the video signal fail or become defective. In such case the aperture in the plate 10 is fully closed. The user is not, therefore, dazzled or the patient subjected to overheating if the camera 5 is disconnected, for example, thereby causing the aperture in the plate 10 to be fully opened.

A joystick or the like may be provided for positioning the measuring window 18.

What is claimed is:

1. Apparatus for adjusting a light source for illuminating an object under examination by means of an endoscope, the apparatus comprising:
   a light source having means for adjusting the quantity of light emitted thereby;
   a light guide connected to said light source for transmitting light therefrom to illuminate said object;
   a video camera for producing a video picture of said object;
   an image guide connected to said camera for transmitting an image of said object thereto;
   a monitor for displaying said video picture; and
   signal processing means connected to said camera for processing the video signal emitted thereby, and also to said monitor, and comprising a window generating device and a window superimposition device for visually displaying and optically defining a window and for generating a measuring window in the video picture displayed by said monitor, and an integrator device connected to said adjusting means and to said window generating device, for integrating a video signal therefrom to adjust the quantity of light emitted by said light source, only within the area of said measuring window.

2. Apparatus as claimed in claim 1, comprising manually operable control means for positioning said measuring window within said video picture and for varying the size of said measuring window.

3. Apparatus as claimed in claim 1, wherein said window superimposition device is adapted to allow said measuring window to be superimposed upon said video picture in the form of a frame.

* * * * *